United States Patent [19]

Ahmed et al.

[11] Patent Number: 4,845,296
[45] Date of Patent: * Jul. 4, 1989

[54] PROCESS FOR PREPARING ALKANOLAMINES

[75] Inventors: Moinuddin Ahmed; James R. Nelson; Charles A. Gibson, all of So. Charleston, W. Va.

[73] Assignee: Union Carbide Corporation, Danbury, Conn.

[*] Notice: The portion of the term of this patent subsequent to Jul. 11, 2006 has been disclaimed.

[21] Appl. No.: 195,395

[22] Filed: May 12, 1988

Related U.S. Application Data

[63] Continuation of Ser. No. 561,045, Dec. 13, 1983, abandoned, which is a continuation-in-part of Ser. No. 247,061, Mar. 24, 1981, abandoned.

[51] Int. Cl.$^4$ .................... C07C 89/02; C07C 85/00; C07C 85/02; C07C 85/18
[52] U.S. Cl. ..................................... 564/477; 564/475
[58] Field of Search ............................... 564/475, 477

[56] References Cited

U.S. PATENT DOCUMENTS

| | | | |
|---|---|---|---|
| 1,904,013 | 8/1927 | Reid et al. | 564/477 |
| 2,196,554 | 4/1940 | Guinot | 564/477 |
| 2,373,199 | 5/1942 | Schwoegler et al. | 564/477 |
| 2,622,099 | 9/1948 | Ferrero et al. | 564/477 |
| 3,151,166 | 9/1964 | Milligan | 564/477 |
| 3,152,188 | 10/1964 | Kirkpatrick et al. | 564/477 |
| 3,544,632 | 12/1970 | Haarer et al. | 564/477 |
| 3,697,598 | 10/1972 | Weibull | 564/477 |
| 3,723,530 | 3/1973 | Goetze et al. | 564/477 |

FOREIGN PATENT DOCUMENTS 513508 10/1939 United Kingdom ................ 564/477

*Primary Examiner*—Floyd D. Higel
*Attorney, Agent, or Firm*—Gerald L. Coon

[57] ABSTRACT

A process is provided for preparing alkanolamines having a high yield of monoalkanolamine which comprises reacting in a reaction mixture an alkylene oxide having from two to four carbon atoms with ammonia in a molar ratio of ammonia to alkylene oxide within the range from about 15.1 to about 50.1 at temperatures above the critical temperature of the reaction mixture and at pressures above the critical pressure of the reaction mixture and high enough to maintain the reaction mixture at sufficiently high fluid densities.

15 Claims, No Drawings

PROCESS FOR PREPARING ALKANOLAMINES

This application is a continuation or prior U.S. application Ser. No. 561,045, filing date Dec. 13, 1983 now abandoned which is a continuation-in-part of application Ser. No. 247,061, filing date Mar. 24, 1981 now abandoned.

BACKGROUND OF THE INVENTION

This invention relates to a process for the preparation of alkanolamines and, more particularly, to a process for preparing alkanolamines with high yields of monoalkanolamine that may be run continuously by the reaction of alkylene oxides with a large excess of ammonia wherein the reaction mixture is maintained in a single supercritical phase.

It is known that alkanolamines, which are used in a variety of commercial applications such as emulsification agents for soaps and cosmetics and as starting materials for the production of raw materials for detergents, wetting agents, emulsifiers, textile auxiliaries and the like, can be obtained by the reaction of alkylene oxides with ammonia or amines, the yield of alkanolamines being a mixture of mono, di-, and trialkanolamines with generally equal relative proportions of the three alkanolamines being frequently obtained. The relative proportions of these three alkanolamines in the product mixture, however, are known to depend on the relative quantities of alkylene oxide and ammonia that are reacted and methods have been used or suggested for achieving higher yields of one or more of the alkanolamines in the mixture by varying the proportion of reactants, such as by increasing the amount of ammonia relative to the alkylene oxide to obtain increased yields of monoalkanolamine, as well as by other process changes.

There is disclosed, for example, in U.S. Pat. No. 2,196,554 to H. M. Guinot a process for preparing mono-hydroxylalkylamines with yields of 90%-95% by reacting at least 30 parts by weight of ammonia with one part of alkylene oxide. Relatively dilute aqueous ammonia solutions are employed and the patent discloses that steam generated during concentration of the reaction mixture is used for heating subsequent reaction mixtures of aqueous ammonia and alklyene oxide to reduce the heat energy requirements for the process.

Another process for preparing alkanolamines with extremely high yields of monoalkanolamines and only small amounts of the di- and trialkanolamines by reacting alkylene oxide with large excess amounts of ammonia in a liquid phase reaction system is disclosed in U.S. Pat. No. 3,697,598 to Weibull et al. The molar ratio of ammonia relative to alkylene oxide used in the process is within the range of 10:1 to 80:1 and the reaction is carried out in the presence of a cation exchange resin catalyst. The process of the patent is described as being a continuous process which is capable of being run isothermally or, preferably, adiabatically at temperatures in the range of from 20° C. to 250° C. when pressures are employed that are high enough to keep the reactants and reaction products in the liquid phase throughout the reaction. There is, however, no disclosure either in the description or in the examples of the patent which suggests that high yields of alkanolamines of any type are obtained when the process is carried out either adiabatically or isothermally without the use of cation exchange resin catalysts, and patentees state that without a cation exchange catalyst it is not possible to realize an adiabatic reaction because it is too slow.

Further, in U.S. Pat. No. 3,723,530 to Goetze et al., there is also disclosed a process for preparing a mixture of alkanolamines by the liquid phase reaction of ethylene oxide and a large excess of ammonia, that is, mole ratios of ammonia to ethylene oxide of from 14 to 40 to one. The patent teaches that when the reaction is carried out in the presence of up to 1 mole of diethanolamine per mole of ethylene oxide, the product obtained will be a mixture of only monoethanolamine and triethanolamine with little or no diethanolamine being present. While the process of the patent is described as being capable of being run continuously either isothermally or adiabatically, the ammonia is usually employed in the form of an aqueous solution, the reaction is carried out in the liquid phase at temperatures in the range of from 60° to 150° and pressures of from 20 to 120 atmospheres, and the monoethanolamine content of the product mixture generally does not exceed 70 percent by weight.

While the processes heretofore disclosed suggest that they are suitable for use in preparing monoethanolamines in high yields by reacting alkylene oxides with excess amount so ammonia, their usefulness in either batch or continuous operations depends on the presence of catalysts or supplemental process steps. It would be highly desirable, however, if a process was available which could be used to readily prepare monoalkanolamines at practical reaction rates that did not involve the potential additional problems associated with catalysts or costs due to complicated or supplemental process steps.

SUMMARY OF THE INVENTION

In accordance with the present invention, there is provided a process for preparing alkanolamines with high yields of monoalkanolamine which comprises reacting in a reaction mixture an alkylene oxide having from two to four carbon atoms with ammonia in a molar ratio of ammonia to alkylene oxide within the range from about 15:1 to about 50:1 at temperatures above the critical temperature of the reaction mixture and at pressures above the critical pressure of the reaction mixture and high enough to maintain the reaction mixture in a single supercritical phase to form a product mixture containing at least about 65% by weight monoalkanolamine. Unreacted ammonia, which is separated from the reaction mixture, may be recycled if desired.

The temperatures employed for carrying out the reaction are preferably as high as possible so that the reaction will proceed at a suitable rate, but generally will be above the critical temperature of the reaction mixture. The process should be high enough to maintain the reaction mixture in a single homogeneous supercritical phase at any point during the process. The density of the reaction mixture, which is primarily dependent upon the pressure employed at the reaction temperature and is an important consideration as to the rate at which the reaction proceeds, should be maintained as high as possible and generally should be at least about 15 lbs./cu. ft. (240 kg/cu.m.). The reaction can be carried out batchwise or continuously under isothermal or, preferably, adiabatic conditions and, while no catalyst is required, the presence of a small amount of water in the reaction mixture has an advantageous catalytic effect.

The term "supercritical phase" as used herein. is defined as the physical state of the reaction mixture wherein both the temperature and pressure conditions are above the critical values thereof in the reaction mixture.

DETAILED DESCRIPTION OF THE INVENTION

The reaction mixture herein described is maintained in a single supercritical phase for the time necessary to form a product mixture composed at least about 65% by weight of monoalkanolamine (generally at least about 75%) and relatively small amounts of di- and trialkanolamine. Unreacted ammonia is separated therefrom by known means. The mono- di-, and trialkanolamines can also be separated from each other, if desired.

The alkylene oxides to which the process of the present invention is applicable are any alkylene oxides having from two to four carbon atoms, including ethylene oxide, propylene oxide, 1,2-butylene oxide, 2,3-butylene oxide, and isobutylene oxide.

In accordance with the present invention, it is essential that a large excess of ammonia is used in the reaction to obtain yields of monoalkanolamines of at least about 65 weight percent. It is advantageous to use about 15 to about 50 moles, and preferably from about 20 to about 35 moles, of ammonia for each mole of alkylene oxide to obtain yields of from about 70 to 80 weight percent. The ammonia should be added to the reaction mixture in a liquid state, generally in a substantially anhydrous condition. The liquid ammonia and alkylene oxide may be premixed just prior to feeding into the reaction vessel or each may be added separately to the reactor.

In accordance with the practice of the invention, it is important that the reaction of alkylene oxide and ammonia be carried out with the reaction mixture in a homogeneous, single supercritical phase. The reaction can be carried out under isothermal conditions; however, it is a particular advantage of this invention that it can also be carried out adiabatically without use of a separate catalyst. The temperature at which the reaction should be carried out is within the range from the critical temperature of the reaction mixture to about 200° C., though the upper limit of the temperature is not crucial. Preferably, the reaction temperature is within the range from the critical temperature of the reaction mixture (generally from about 135° C.) to about 180° C. The critical temperature is selected as the minimum temperature since that is about the temperature at which the reaction proceeds sufficiently rapidly to be commercially advantageous. Under isothermal conditions, since the reaction is strongly exothermic, it is necessary to withdraw heat from the reaction mixture to keep the temperature approximately constant.

In the case when the reaction is to be carried out under adiabatic or nearly adiabtatic conditions, the reactants are preheated before they are introduced into the reactor. Because of the reaction heat involved, any selected initial reaction temperature is rapidly increased and the initial reaction temperatures should be chosen so that the maximum desired temperature will be obtained during the period of residence of the reaction mixture within the reactor. The preferred maximum temperature is between about 170° C. and 180° C., though the higher the reaction temperature, the higher the pressure that is necessary to maintain the density of the reaction mixture as high as possible.

At such reaction temperatures, it is essential that the pressures imposed on the system are high enough to maintain the reaction mixture in a single supercritical phase. In any case, the reaction pressure should be at least as high as the critical pressure of the reaction mixture at any point encountered during the process. Preferably, the pressures imposed on the system are within the range from about 170 to about 240 atmospheres. The latter is a practical upper limit and is not crucial.

As pointed out hereinabove, the reaction mixture should be maintained at supercritical conditions to ensure that only one phase is present at sufficiently high temperatures and densities to permit the reaction to proceed at a suitable rate. The possible existence of two phases (vapor and liquid) at subcritical conditions is disadvantageous because (1) the ratios of ammonia and alkylene oxide will not be equivalent in the two phases due to their differences in volatilities, and (2) the low density vapor phase takes up valuable space in the reactor. The first disadvantage manifests itself by reducing the percent monoalkanolamine formed, because the liquid phase, where the vast majority of the reaction takes place, has been somewhat depleted of ammonia. Therefore, the effective ammonia to alkylene oxide mole ratio has been reduced.

The density of the reaction mixture should be maintained above the critical denisty (i.e., the density at the critical temperature and critical pressure) and, in general, should be at least about 15 lbs/cu.ft. (240 kg/cu.m). Preferably, the density of the reaction mixture should be maintained in the range of from about 21 to about 28 lbs.cu.ft. or even higher if practical, to enhance reaction rates. (Reaction rates are proportional to the density raised to the third power). Among the process variables, pressure has the most important influence on density, and operating at supercritical pressures is required to attain these desired densities, at the desired reaction temperatures. The mole ratio of ammonia and alkylene oxide reactants, and temperature also impact upon the density of the reaction mixture.

While it is not essential that the process of the invention be carried out in the presence of any catalyst, advantageous embodiments of the process of the invention may be carried out with a small amount of water incorporated in the reaction mixture along with the alkylene oxide and ammonia reactants. It has been found that the presence of small amounts of water in the reaction mixture has an advantageous catalytic effect on the reaction rate for forming alkanolamines, though it does not appear to affect the yield of monoalkanolamine in the product mixture. The amount of water that is present is not crucial, and only small amounts of water may achieve the catalytic affect that is desired. In general, from about 0.5 percent up to about 5 percent by weight of water, based on the weight of the reaction mixture, need be present. Amounts of water greatly in excess of that which may be catalytically useful, however, should be avoided to limit the energy requirements needed to separate water from the product mixture.

After conclusion of the reaction, substantially all of the alkylene oxide has been reacted and the unreacted ammonia may be separated from the product mixture by any means known in the art, such as by reducing the pressure sufficiently to vaporize the ammonia so that it can be separated as a gas. The ammonia can then be recycled, if desired, by repressurizing to a liquid phase before mixing with fresh alkylene oxide. The unreacted ammonia may also be separated from the product mixture by distilling under pressure. The alkanolamine analogues in the product mixture may also be separated by known distillation methods, or the product mixture may be used as a starting material for the preparation of other organic amines.

As pointed out hereinabove, the process of the invention may be carried out batchwise or continuously, either under isothermal or adiabatic conditions. In an alternate embodiment of the process of the invention which is run continuously, the ammonia and alkylene oxide reactants in the molar ratios hereinabove described are continuously fed, either separately or, preferably, as a mixture, to a tubular reactor which is capable of operating as efficiently as possible as a plug-flow reactor having means for providing the pressures needed to maintain the reaction mixture in a single supercritical phase. The reaction may be carried out isothermally in a tubular reactor having cooling means or, advantageously, under adiabatic conditions where the reactants are preheated to a temperature, for example, between about 100° C. to 130° C. Such a continuous process is described in co-pending application Ser. No. 196,802, filed May 16, 1988, which is a continuation of application Ser. No. 561,046, filed Dec. 13, 1983, now abandoned, and which is a continuation-in-part of application Ser. No. 259,899, filed May 4, 1981 now abandoned. Small amounts of water may also be added to the reaction mixture, if desired.

The residence time of the reaction mixture in said adiabatic reactor should be sufficiently high to permit the reaction to proceed to completion, generally in less than about ½ hour. At the completion of the reaction, that is, when essentially all the alkylene oxide has been reacted, the unreacted ammonia is separated from the product mixture as hereinabove described and recycled to the reactor. The recycled ammonia is pressurized to a liquid state prior to mixing with the alkylene oxide and fresh make-up ammonia. The product mixture which is obtained can be separated into alkanolamine components by distillation methods known in the art or can be used as a starting material for the production of materials such a organic polyamines.

This invention will become more clear when considered together with the following examples which are set forth as being merely illustrative of the invention and which are not intended in any manner, to be limitative thereof. Unless otherwise indicated, all parts and percentages are by weight.

EXAMPLE 1

A 2 liter (1984 ml.) stainless steel autoclave having a high speed agitator and equipped with charging, sampling, and temperature control means was used in carrying out the reaction runs of this example. A series of reactions was run using liquid anhydrous ammonia, water, and ethylene oxide in the proportions reported in Table I. The ammonia and water were charged to the autoclave which was evacuated to a pressure of about 1 mm Hg absolute and then with vigorous agitation were heated to 170° C. The ethylene oxide was then charged to the autoclave and, with vigorous agitation, the reaction temperature was maintained at 170° C. for 30 minutes. A sample of the reaction mixture was taken after the time indicated in Table I during each of the reaction runs of this example. After 30 minutes, the reaction mixture was cooled to below 50° C. and unreated ammonia was vented from the autoclave until the pressure in the autoclave indicated essentially complete removal of gas. The liquid product mixture was then drained from the autoclave and the composition thereof was determined by gas chromatographic analysis.

The amounts of ammonia and ethylene oxide reactants used were intended to obtain an average ammonia to ethylene oxide mole ratio of 25:1 for each of the reaction runs of this example. The average density of the reaction mixture during each of the reaction runs of this example was 24 lbs./cu. ft.

A summary of the proportion of ingredients, reaction conditions and composition of the product mixtures for each of the reaction runs of this example is reported in Table I.

It is apparent from results shown in Table I that an alkanolamine mixture was prepared with a high yield of monoalkanolamine during each of the runs of this example.

TABLE I

| | Ammonia | | Ethylene Oxide | | Water | | Sample Time | Press. | Ethylene Oxide | Product Distribution Wt %[a] | | |
|---|---|---|---|---|---|---|---|---|---|---|---|---|
| Run | Moles | Grams | Moles | Grams | Moles | Grams | (Min) | PSIG | Residual Mol % | MEA | DEA | TEA |
| 1 | 39.81 | 678 | 1.57 | 69.1 | 0.754 | 13.57 | 0 | 3250 | — | 73.21 | 22.50 | 4.74 |
| | | | | | | | 15 | 2850 | 0.012 | 73.21 | 22.04 | 4.74 |
| 2 | 39.81 | 678 | 1.57 | 69.1 | 0.754 | 13.57 | 0 | 3310 | — | | | |
| | | | | | | | 15 | 2800 | 0.012 | 75.53 | 20.20 | 4.27 |
| 3 | 39.81 | 678 | 1.62 | 71.4 | 0.754 | 13.57 | 0 | 3300 | — | | | |
| | | | | | | | 12 | 2800 | 0.041 | 75.24 | 20.34 | 4.42 |
| 4 | 39.81 | 678 | 1.62 | 71.3 | 0.754 | 13.57 | 0 | 3210 | — | | | |
| | | | | | | | 12 | 2800 | 0.025 | 74.54 | 20.90 | 4.55 |
| 5 | 39.81 | 678 | 1.59 | 70.0 | 0.754 | 13.57 | 0 | 3500 | — | | | |
| | | | | | | | 9 | 2820 | 0.096 | 75.36 | 20.17 | 4.47 |
| 6 | 39.81 | 678 | 1.57 | 69.1 | 0.754 | 13.57 | 0 | 3500 | — | | | |
| | | | | | | | 9 | 2950 | 0.14 | 76.12 | 19.96 | 3.89 |
| 7 | 39.81 | 678 | 1.58 | 69.5 | 0.754 | 13.57 | 0 | 3410 | — | | | |
| | | | | | | | 6 | 2800 | 0.55 | 74.68 | 21.04 | 4.28 |
| 8 | 39.81 | 678 | 1.62 | 71.3 | 0.754 | 13.57 | 0 | 3450 | — | | | |
| | | | | | | | 3 | 2900 | 1.74 | 76.03 | 19.96 | 3.99 |
| 9 | 39.81 | 678 | 1.62 | 71.3 | 0.754 | 13.67 | 0 | 3250 | — | | | |
| | | | | | | | 3 | 3050 | 1.96 | | | |
| 10 | 39.81 | 678 | 1.59 | 70.1 | 0.754 | 13.57 | 0 | 3300 | — | 73.21 | 22.04 | 4.74 |
| | | | | | | | 25 | 2700 | | | | |

[a]After a total reaction time of 30 minutes.

EXAMPLE 2

Using the apparatus and procedure of Example 1, a series of reaction runs was carried out to demonstrate the effect of reaction product density and ammonia to ethylene oxide mole ratio on the reaction rate and distribution of alkanolamines in the product mixture. Runs 1 to 8 were carried out with an average ammonia to ethylene oxide mole ratio of 30 to 1 and runs 9 to 12 use a mole ratio of 25 to 1. Runs 1 to 4 and 9 to 12 were carried out at an average density of 22 lbs/cu. ft and Runs 5 to 8 were carried out at an average density of 24 lbs/cu. ft. A sample of the reaction mixture was taken from the reactor during each reaction run.

The proportion of ingredients, temperature and pressure conditions and analysis results (used analytical procedures described in example 1) for each of the reactions runs of this Example are summarized in Table II.

It is apparent from the results shown in Table II that an ethanolamine product mixture containing high yields of monoethanolamine was prepared during each reaction run of this example. The reaction rate for each of the runs would be suitable but the results show that the reaction rate for runs 1 to 4, which were maintained at an average density of 22 lbs/cu. ft., was somewhat slower than the reaction rate for runs 5 to 8, which were maintained at an average density of 24 lbs/cu.ft.

TABLE III

| Sample Number | Time, Minutes from EO Injection | % Conversion Based on Residual EO |
|---|---|---|
| 1 | 3 | 74.9 |
| 2 | 6 | 77.2 |
| 3 | 9 | 92.3 |
| 4 | 24 | 100.0 |

After 30 minutes from the time ethylene oxide was added, the mixture in the autoclave was cooled to below 50° C. and the unreacted ammonia was separated from the product mixture. The liquid product mixture was discharged from the autoclave and analyzed for alkanolamine composition by gas chromatography. The product mixture was determined to contain 84.03 percent monoethanolamine, 14.36 percent diethanolamine, and 1.60 percent triethanolamine.

To demonstrate the need for supercritical temperatures, the following reaction run was carried out in the autoclave reactor described in Example 1 at a subcritical temperature of 120° C. The pressure of 2000 psig ensured one-phase operation, and the fluid density was 32 lbs/cu.ft.

In this control, a mixture of 678 grams (39.81 moles)

TABLE II

| Run | Ammonia Moles | Ammonia Grams | Ethylene Oxide Moles | Ethylene Oxide Moles | Water Moles | Water Grams | Density lbs/ft³ | Time (Min) | Temp. °C. | Press. PSIG | Ethylene Oxide Residual Mol % | MEA | DEA | TEA |
|---|---|---|---|---|---|---|---|---|---|---|---|---|---|---|
| 1 | 37.05 | 631 | 1.20 | 52.8 | 0.70 | 12.6 | 21.89 | 0 | 169 | 2900 | — | | | |
| | | | | | | | | 4 | 170 | 2800 | 1.59 | 75.97 | 19.37 | 4.66 |
| 2 | 37.05 | 631 | 1.23 | 54.4 | 0.70 | 12.6 | 21.94 | 0 | 170 | 3020 | — | | | |
| | | | | | | | | 8 | 173 | 2860 | 0.53 | 76.01 | 19.30 | 4.69 |
| 3 | 37.05 | 631 | 1.26 | 55.44 | 0.70 | 12.6 | 21.98 | 0 | 171 | 3050 | — | | | |
| | | | | | | | | 14 | 170 | 2600 | 0.11 | — | — | — |
| 4 | 37.05 | 631 | 1.23 | 54.4 | 0.70 | 12.6 | 21.94 | 0 | 170 | 2800 | — | | | |
| | | | | | | | | 18 | 170 | 2560 | 0.07 | 81.02 | 15.57 | 3.4 |
| 5 | 40.42 | 688 | 1.36 | 59.8 | 0.74 | 13.7 | 23.95 | 0 | 170 | 3100 | — | | | |
| | | | | | | | | 4 | 172 | 3100 | 1.14 | 76.12 | 19.24 | 4.64 |
| 6 | 40.16 | 684 | 1.40 | 61.6 | 0.74 | 13.7 | 23.87 | 0 | 170 | 3300 | — | | | |
| | | | | | | | | 8 | 172.5 | 2940 | 0.16 | — | — | — |
| 7 | 40.98 | 698 | 1.32 | 58.1 | 0.74 | 13.7 | 24.2 | 0 | 170 | 3450 | — | | | |
| | | | | | | | | 12 | 171 | 3240 | 0.03 | 82.67 | 14.56 | 2.76 |
| 8 | 40.42 | 688.4 | 1.35 | 59.4 | 0.74 | 13.7 | 23.94 | 0 | 170 | 3350 | — | | | |
| | | | | | | | | 14 | 171 | 3000 | 0.015 | 76.97 | 18.94 | 4.09 |
| 9 | 36.41 | 620 | 1.45 | 63.8 | 0.69 | 12.4 | 21.89 | 0 | 181 | 3700 | — | | | |
| | | | | | | | | 4 | 180 | 3000 | 0.61 | 73.32 | 21.24 | 5.44 |
| 10 | 36.41 | 620 | 1.45 | 63.7 | 0.69 | 12.4 | 21.88 | 0 | 179 | 3400 | — | | | |
| | | | | | | | | 8 | 179 | 2950 | 0.13 | — | — | — |
| 11 | 36.76 | 626 | 1.46 | 64.2 | 0.69 | 12.4 | 22.09 | 0 | 184 | 3700 | — | | | |
| | | | | | | | | 12 | 178 | 2980 | 0.015 | 74.91 | 20.2 | 4.89 |
| 12 | 36.41 | 620 | 1.45 | 64.0 | 0.69 | 12.4 | 21.89 | 0 | 180 | 3625 | — | | | |
| | | | | | | | | 16 | 179.5 | 3010 | 0.01 | 74.07 | 20.78 | 5.15 |

(a)After a total reaction time of 30 minutes.

EXAMPLE 3

A mixture of 786.4 grams (46.2 moles) of ammonia and 15.7 grams of water was charged to the stirred autoclave described in Example 1 which had previously been evacuated to about one millimeter of Hg vacuum. The mixture was heated to 170° C. and 3900 psig with stirring and 54.1 grams (1.23 moles) of ethylene oxide were injected into the stirred mixture. The density of the reaction mixture was maintained at an average of 27 lbs./cu. ft.

Small samples of the reaction mixture were periodically removed from the autoclave and analyzed by mass spectrometry for residual ethylene oxide and the sample times and conversion of ethylene oxide are shown below in Table III.

of ammonia and 13.57 grams of water was charged to the evacuated, stirred autoclave of Example 1 and heated to 120° C. Nitrogen gas was added to the autoclave until a pressure of 2000 psig was obtained. Ethylene oxide (72.98 grams, 1.659 moles) was injected into the stirred mixture in the autoclave and the temperature was maintained at 120° C. during the entire run.

Small samples were periodically removed from the autoclave reactor and analyzed by mass spectrometry for residual ethylene oxide and the results are summarized in Table IV, below.

TABLE IV

| Sample Number | Time, Minutes from EO Injection | % Conversion Based on Residual EO |
|---|---|---|
| 1 | 5 | 16.25 |
| 2 | 10 | 33.00 |
| 3 | 15 | 35.25 |
| 4 | 20 | 56.00 |

TABLE IV-continued

| Sample Number | Time, Minutes from EO Injection | % Conversion Based on Residual EO |
|---|---|---|
| 5 | 25 | 73.00 |
| 6 | 30 | 82.75 |
| 7 | 40 | 92.50 |

The reaction was continued at 120° C. for an additional 138 minutes, after which the mixture was cooled, unreacted ammonia was separated therefrom, and the liquid product mixture was recovered and analyzed by gas chromatography.

The product mixture was determined to contain 74.44 percent of monoethanolamine, 21.17 percent diethanolamine, and 4.38 percent triethanolamine. While the liquid phase reaction resulted in high yields of monoethanolamine, the reaction rate was determined to be too slow to be suitable.

What is claimed is:

1. A process for preparing alkanolamines having a high yield of monoalkanolamine which comprises reacting in a reaction mixture an alkylene oxide having from two to four carbon atoms with ammonia in a molar ratio of ammonia to alkylene oxide within the range from about 15:1 to about 50:1 at temperatures above the critical temperature of the reaction mixture and at pressures above the critical pressure of the reaction mixture and high enough to maintain the reaction mixture in a single supercritical phase to form a product mixture containing at least about 65% by weight monoalkanolamine.

2. The process of claim 1 wherein the density of the reaction mixture is above 15 lbs./cu. ft.

3. The process of claim 1 wherein the reaction is carried out in the presence of a small, catalytically effective amount of water.

4. The process of claim 1 wherein the reaction temperature is above 135° C.

5. The process of claim 1 wherein the reaction is carried out at pressures in the range from about 170 to 240 atmospheres.

6. The process of claim 5 wherein the density of the reaction mixture is in the range from about 21 to about 28 lbs./cu. ft.

7. The process of claim 1 wherein the reaction temperature is in the range from the critical temperature of the reaction mixture to about 180° C.

8. The process of claim 6 wherein the reaction temperature is in the range from the critical temperature of the reaction mixture to about 180° C.

9. The process of claim 8 wherein the reaction is carried out in the presence of a small, catalytically effective amount of water.

10. The process of claim 9 wherein the process is carried out adiabatically.

11. The process of claim 1 wherein unreacted ammonia is separated from the product mixture.

12. The process of claim 1 wherein the product mixture contains at least about 75% by weight monoethanolamine.

13. The process of claim 3 wherein the density of the reaction mixture is in the range from about 21 to about 28 lbs./cu. ft.

14. The process of claim 13 wherein the reaction is carried out in the presence of from about 0.5 to 5 percent by weight of water based on the weight of the reaction mixture.

15. A process for preparing alkanolamines having a high yield of monoalkanolamine which comprises reacting an alkylene oxide having from two to four carbon atoms with ammonia in a molar ratio of ammonia to alkylene oxide within the range from about 15:1 to about 50:1 at temperatures at which the reaction proceeds above about 100° C., and at pressures high enough to maintain the reaction mixture in a single supercritical fluid phase to form a product mixture containing predominantly monoalkanolamine.

* * * * *